United States Patent
Schuler

(10) Patent No.: US 9,254,388 B2
(45) Date of Patent: Feb. 9, 2016

(54) METHOD AND SYSTEM FOR REGULATION OF ENDOCRINE AND EXOCRINE GLANDS BY MEANS OF NEURO-ELECTRICAL CODED SIGNALS

(71) Applicant: Eleanor Schuler, Rio Rancho, NM (US)

(72) Inventor: Eleanor Schuler, Rio Rancho, NM (US)

(73) Assignee: Codes of Life, LLC, Albuquerque, NM (US)

( * ) Notice: Subject to any disclaimer, the term of this patent is extended or adjusted under 35 U.S.C. 154(b) by 0 days.

(21) Appl. No.: 14/258,101

(22) Filed: Apr. 22, 2014

(65) Prior Publication Data

US 2015/0297895 A1 Oct. 22, 2015

Related U.S. Application Data

(63) Continuation of application No. 12/552,928, filed on Sep. 2, 2009, now Pat. No. 8,818,502, which is a continuation of application No. 11/401,734, filed on Apr. 10, 2006, now Pat. No. 7,725,176, which is a continuation-in-part of application No. 10/889,407, filed on Jul. 12, 2004, now Pat. No. 7,058,446.

(60) Provisional application No. 60/486,089, filed on Jul. 10, 2003.

(51) Int. Cl.
*A61N 1/40* (2006.01)
*A61N 1/36* (2006.01)

(52) U.S. Cl.
CPC .......... *A61N 1/36139* (2013.01); *A61N 1/3606* (2013.01)

(58) Field of Classification Search
None
See application file for complete search history.

(56) References Cited

U.S. PATENT DOCUMENTS

| | | | |
|---|---|---|---|
| 5,231,988 A | 8/1993 | Wernicke et al. | |
| 6,171,239 B1 | 1/2001 | Humphrey | |
| 6,775,573 B2 * | 8/2004 | Schuler et al. | 607/40 |
| 6,826,428 B1 | 11/2004 | Chen et al. | |
| 6,853,862 B1 * | 2/2005 | Marchal et al. | 607/40 |
| 7,058,446 B2 * | 6/2006 | Schuler et al. | 607/2 |
| 7,308,302 B1 | 12/2007 | Schuler et al. | |
| 7,725,176 B2 | 5/2010 | Schuler et al. | |
| 2002/0010499 A1 * | 1/2002 | Rigaux et al. | 607/62 |
| 2003/0045909 A1 | 3/2003 | Gross et al. | |
| 2003/0055467 A1 | 3/2003 | Ben-Haim et al. | |

(Continued)

FOREIGN PATENT DOCUMENTS

| | | |
|---|---|---|
| EP | 0569522 B1 | 6/1999 |
| WO | WO 02/04068 A1 | 1/2002 |

*Primary Examiner* — Carl H Layno
*Assistant Examiner* — Ankit Tejani
(74) *Attorney, Agent, or Firm* — Kermit D. Lopez; Luis M. Ortiz; Ortiz & Lopez, PLLC

(57) ABSTRACT

Methods, systems, and devices for endocrine and exocrine gland control, Neuro-electrical coded signals can be selected from a storage area that is representative of body organ function. The selected neuro-electrical coded signals are then transmitted to a treatment member, which is in direct contact with the body, and which then broadcasts the neuro-electrical coded signals to a specific endocrine and exocrine gland nerve or gland to modulate the gland functioning. A control module is provided for transmission to the treatment member. The control module contains the neuro-electrical coded signals which are selected and transmitted to the treatment member, and computer storage can be provided for greater storage capacity and manipulation of the neuro-electrical coded signals.

14 Claims, 2 Drawing Sheets

(56) References Cited

U.S. PATENT DOCUMENTS

| | | |
|---|---|---|
| 2003/0208242 A1 | 11/2003 | Harel et al. |
| 2003/0212439 A1 | 11/2003 | Schuler et al. |
| 2004/0098062 A1* | 5/2004 | Nachum ................... 607/40 |
| 2004/0143296 A1 | 7/2004 | Wang et al. |
| 2005/0153885 A1 | 7/2005 | Yun et al. |
| 2005/0192644 A1 | 9/2005 | Boveja et al. |

\* cited by examiner

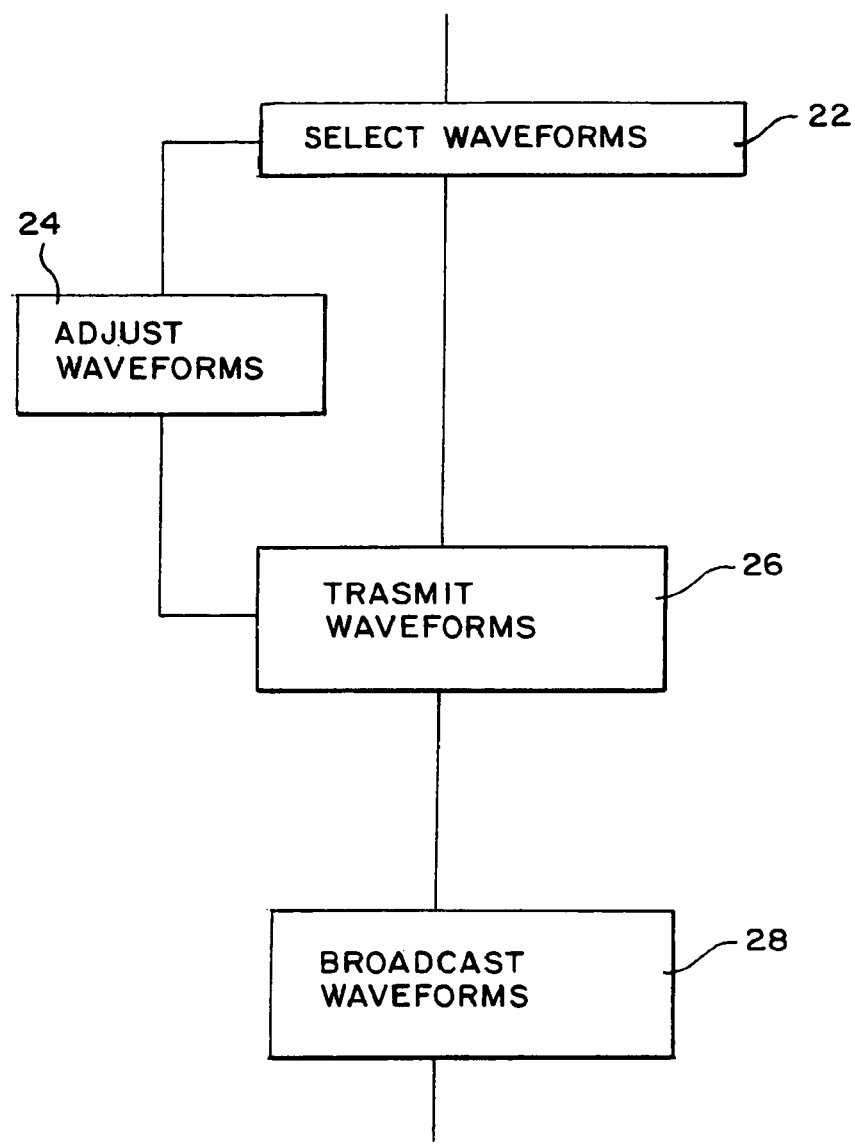

METHOD AND SYSTEM FOR REGULATION OF ENDOCRINE AND EXOCRINE GLANDS BY MEANS OF NEURO-ELECTRICAL CODED SIGNALS

CROSS-REFERENCE AND PRIORITY TO PATENT APPLICATIONS

This patent application is a continuation of U.S. patent application Ser. No. 12/552,928, entitled "Method and System for Regulation of Endocrine and Exocrine Glands by Means of Neuro-Electrical Coded Signals," which was filed on Sep. 2, 2009 and issued as U.S. Pat. No. 8,818,582 on Aug. 26, 2014, and is incorporated herein by reference in its entirety. U.S. patent application Ser. No. 12/552,928 is a continuation of U.S. patent application Ser. No. 11/401,734, which issued as U.S. Pat. No. 7,725,176, which is a Continuation-in-Part of U.S. patent application Ser. No. 10/889,407, which issued as U.S. Pat. No. 7,058,446, and which in turn is a continuation of U.S. Provisional Patent Application Ser. No. 60/486,089, which was filed on Jul. 10, 2003 and entitled "Regulation of Endocrine and Exocrine Glands by Means of Neuro-Coded Signals." The aforementioned patent applications are incorporated herein by reference in their entireties. This patent application therefore claims priority to the Jul. 10, 2003 filing date of U.S. Provisional Patent Application Ser. No. 60/486,089.

FIELD OF THE INVENTION

Embodiments are generally related to the regulation of endocrine and exocrine glands utilizing neuro-electrical coded signals.

BACKGROUND

Bodily homeostasis is the regulation of the milieu interieur (internal environment) of the living mammalian body. Homeostasis is the process through which organs, glands, and the central and peripheral nervous system harmoniously function to balance life equilibrium. The process includes, but is not limited to, glandular participation in the regulation of body temperature, heart rate, respiration, digestion, energy metabolism, immunity, and reproduction. Glandular secretions also are used to protect the human or animal body from invading microbes, environmental dust, and other wind carried or propelled chemicals, smoke products or odors.

The glandular flow of chemicals or hormones plays an important role in the homeostasis process. There are two principal classes of secretory glands. There are the "endocrine" glands that secrete directly into the blood stream and there are the "exocrine" glands that produce a secretion onto the surface of the body and to protect with secretions in the exterior orifices or into the interior of organs other than directly into the bloodstream.

The ability to electrically cause the endocrine or exocrine glands to secrete or to cease secreting or even to partially secrete would be a compelling medical technology for potentially controlling or adjusting body homeostasis. The control of the glands is by means of neuro-electrical coded signals that originate in the brain and brain stem. The ability to influence the amount of chemicals, hormones or aqueous/mucoid substances to influence the body's response to stress, sexual function, lactation, tears, digestive juices, salt & water balance and behavior. Puberty is evolved in male and female mammals because of the long-term influence of endocrine glands. If such system of glands is controlled by actual neuro-electrical coded signals (waveform) generated by a device that records, stores, and rebroadcasts it would greatly add to the clinical medicine tools. Such glandular control technology would provide a clinical neuro-electric method to fine-tune the function of many glandular based biological systems for the benefit of mankind.

The invention would use the actual neuro-electrical coded signals that send operational information to operate and regulate the wide variety of endocrine and exocrine glands of the human and animal body. These actual neuron signals travel along selected nerves to send the operational commands to the target gland.

The glands of the human and other mammals are operated by neuro-electrical coded signals from the brain which, in turn can excrete, in selected cases, chemical instructional signals. These chemical signals are transferred to target organs via the blood stream in the case of the endocrine glands.

The exocrine glands do not excrete into the blood stream as do the endocrine glands. These types of glands have a type of duct system to flow the secretions outward. The exocrine glands excrete or secrete largely onto surfaces exterior to the body such as the sweat glands which help cool the body as a contribution to body homeostasis. The sebaceous glands lubricate the surface of the skin with an oily substance. The lacrimal glands make tears to cleanse and lubricate the eyes. Important exocrine glands are the mammary glands, which provide babies milk. The class of species called "mammals" gets their name because they nurse their young from mammary glands.

Another type of exocrine glands are those that provide digestive chemicals such as saliva and digestive juices that affect the mouth, stomach, and intestines to begin as the first step to accomplish the digestion of food. There are wax producing glands in the external ear canal for protection from insects and microbes.

An example of an exocrine gland in a non-mammal species is the poison gland in snakes which is injected via fangs into a victim, which is usually a mammal, as an aid in catching food and to begin the digestive process.

This is a representative sampling of the endocrine glands which can be regulated by neuro-electrical coded signals. These glands are ductless and transfer their secretory hormone products directly into the blood stream. The blood stream carries the endocrine hormones to distant cells or target organs within the body to control short or long-term functions. The following list is not meant to be complete or all encompassing, but to provide a picture of the arena in which the invention operates.

Endocrine glands include the pituitary, thyroid, adrenal, parathyroid, ovary, testis, and part of the pancreas. There is also the placenta, thymus, and pineal gland. The prostate may be considered an exocrine gland. The lubricating vaginal canal mucous produced by the adult female in response to sexual stimulation can be considered an exocrine gland. The protective mucus produced in the bronchial tubes of the respiratory tract also qualifies as exocrine type.

The kidney is also an excretory gland plus a vital organ. It produces hormones involved in the control of blood pressure and for erythropoiesis which is the production of red blood cells. The kidney also functions as a vital organ filter to remove soluble waste products from the blood stream. Therefore the kidney is part a method to remove certain liquid waste and it is an endocrine gland too.

The endocrine and exocrine glandular operating signal(s) occur naturally as a burst or continuous pattern of signals followed by a pause and then another burst of neuron activity followed by a pause of short or long duration and so it is on and on throughout life. Such signal(s) amplitude or time of pause can be varied to accomplish the glandular activity required. Endocrine and exocrine glandular activity requires variable repetitive neuro-electrical coded signals as humans or animals live. Various glandular secretions operate in a symphonic pattern being conduced by the brain to accomplish the mission assigned, all aimed at maintaining the best body homeostasis. There is adequate but variable space between the signals produced by the neurons located both in the brain and the peripheral nervous system to allow synchronization of secretion production into smooth hormonal or chemical applications by the endocrine and exocrine glands.

SUMMARY

The following summary is provided to facilitate an understanding of some of the innovative features unique to the present invention and is not intended to be a full description. A full appreciation of the various aspects of the embodiments disclosed herein can be gained by taking the entire specification, claims, drawings, and abstract as a whole.

The invention provides a method for controlling endocrine and exocrine glands. Stored neuro-electrical coded signals that are generated and carried in the body are selected from a storage area. The selected waveforms are then transmitted to a treatment member who is in direct contact with the body. The treatment member then broadcasts the selected neuro-electrical coded signals to a nerve or endocrine gland or exocrine gland directly in the body.

The neuro-electrical coded signals may be selected from a storage area in a computer, such as a scientific computer. The process of transmitting the selected neuro-electrical coded signals can either be done remotely or with the treatment member connected to a control module. The transmission may be seismic, electronic, the use of an antenna, or via any other suitable method.

The invention further provides an apparatus for controlling endocrine and exocrine glands. The apparatus includes a source of collected neuro-electrical coded signals that are indicative of endocrine and exocrine glands functioning, a treatment member in direct contact with the body, means for transmitting collected waveforms to the treatment member, and means for broadcasting the collected neuro-electrical coded signals from the treatment member to the endocrine and/or exocrine glands.

The transmitting means may include a digital to analog converter. The source of collected waveforms preferably comprises a computer which has the collected waveforms stored in digital format. The signals or wave forms can be collected from living subjects via an analog-to-digital converter and stored in a memory of a suitable digital computing device. The computer may include separate storage areas for collected neuro-electrical coded signals of different categories.

The treatment member may be comprised of an antenna or an electrode, or any other means of broadcasting one or more neuro-electrical coded signals directly to the body.

BRIEF DESCRIPTION OF THE FIGURES

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

The invention is described in greater detail in the following description of examples embodying the best mode of the invention, taken in conjunction with the drawing figures, in which:

FIG. 3 illustrates a flow chart of the method according to the disclosed embodiments.

DETAILED DESCRIPTION

Figure 1:
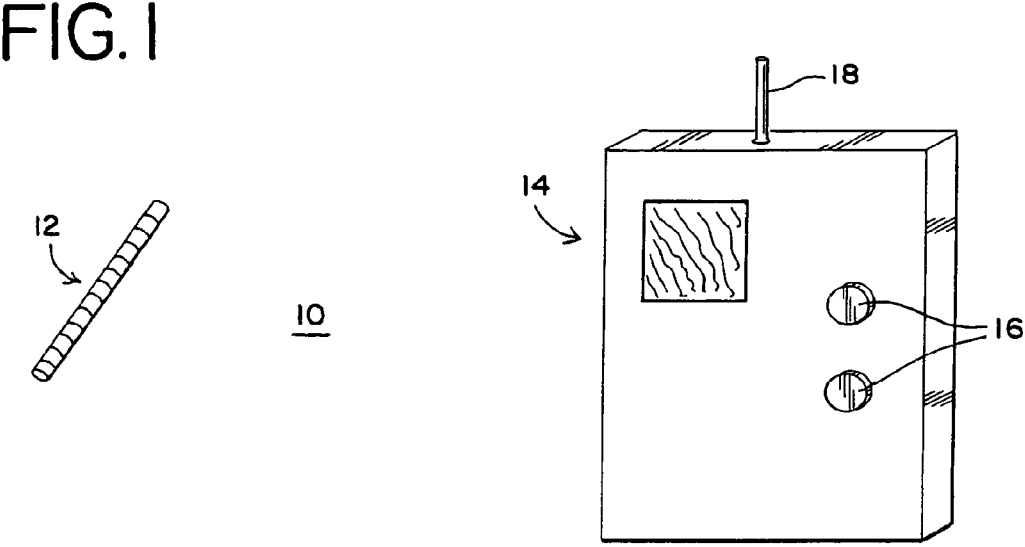
FIG. 1 illustrates a schematic diagram of one form of apparatus for practicing the method according to the disclosed embodiments.

The particular values and configurations discussed in these non-limiting examples can be varied and are cited merely to illustrate at least one embodiment and are not intended to limit the scope thereof.

For the purpose of promoting an understanding of the principles of the invention, references will be made to the embodiments illustrated in the drawings. It will, nevertheless, be understood that no limitation of the scope of the invention is thereby intended, such alterations and further modifications in the illustrated device, and such further applications of the principles of the invention illustrated herein being contemplated as would normally occur to the one skilled in the art to which the invention relates.

Skin usually has a 1000 to 30,000 ohm resistance while the interior of the body is quite conductive. All coded signals operate at less than 1 volt, naturally. Applied voltage may be up to 20 volts according to the invention to allow for voltage loss during the transmission or conduction of the required coded signals through mylin nerve sheath or resistive fat and other material. Current should always be less than 2 amps output for the invention. Direct conduction into the nerves via electrodes connected directly to such nerves will likely have outputs of less than 3 volts and current of less than one-tenth of an amp. Up to 10 or more channels may be used simultaneously to exert medical treatment on glandular control to aid a patient in moving or performing muscular tasks suitable to his or her well-being as medical treatment.

The invention encompasses both a device and a method for endocrine and exocrine gland control by means of neuro-electrical coded signals. One form of a device 10 for endocrine and exocrine gland control, as shown in FIG. 1, is comprised of at least one treatment member 12 and a control module 14. The treatment member 12 is in direct contact with a body and receives a neuro-electrical coded signal from the control module 14. The treatment member 12 may be an electrode, antenna, a seismic transducer, or any other suitable form of conduction attachment for broadcasting endocrine and exocrine gland signals that regulate or operate glandular function in human or animals. The treatment member 12 may be attached to efferent nerves leading to the endocrine and exocrine glands, afferent nerves leading to the brain or brainstem to accomplish modulation of glandular output, the cervical spine, the neck, or the endocrine and exocrine glands in a surgical process. Such surgery may be accomplished with "key-hole" entrance in a thoracic or limb stereo-scope procedure. If necessary, a more expansive thoracotomy approach may be required for more proper placement of the treatment member 12. Neuro-electrical coded signals known to modulate endocrine and exocrine gland function may then be sent into nerves that are in close proximity with the brain stem or other parts of the brain, or in nerve plexi or junctions of nerves any wherein in the body that are appropriate to regulate glands.

The control module 14 includes at least one control 16 and an antenna 18. The control 16 allows the device to regulate the signal transmission into the body. As shown in FIG. 1, the control module 14 and treatment member 12 can be entirely separate elements allowing the device 10 to be operated remotely. The control module 14 can be unique, or can be any appropriate conventional device which can provide neuro-electrical coded signals for transmission to the treatment member 12.

Figure 2:
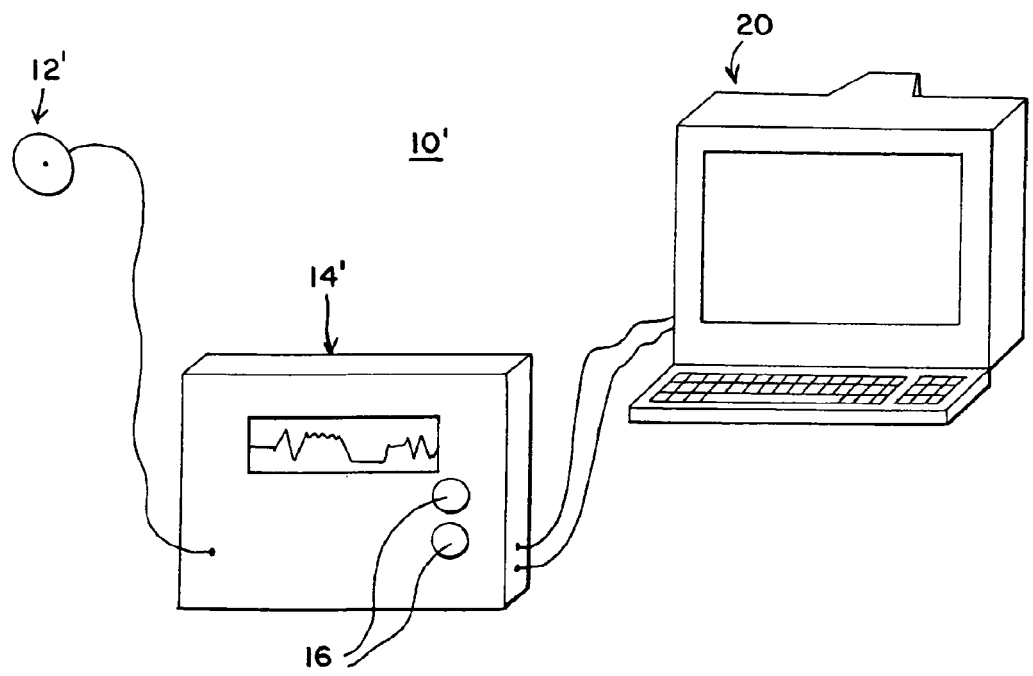
FIG. 2 illustrates a schematic diagram of another form of apparatus for practicing the method according to the disclosed embodiments.

In an alternate embodiment of the device 10, as shown in FIG. 2, the control module 14' and treatment member 12' are connected. Similar members retain the same reference numerals in this figure. Additionally, FIG. 2 further shows another embodiment of the device 10' as being connected to a computer 20, which provides greater capacity to store the neuro-electrical coded signals. The output voltage and amperage provided by the device 10' during treatment shall not exceed 20 volts or 2 amps for each signal.

The computer 20 is used to store the library of unique neuro-electrical coded signals, which have been recorded from mammals. Such signals are complex and unique to the endocrine and exocrine glands. It is a neuro-electrical coded-signal(s) selected from the stored library of neuro-electrical coded signals (waveforms) in the computer 20 which is transmitted to the control module 14' and used for treatment of a patient. The waveform signals, and their creation, are described in greater detail in U.S. patent application Ser. No. 10/000,005, filed Nov. 20, 2001, and entitled "Device and Method to Record, Store and Broadcast Specific Brain Waveforms to Modulate Body Organ Functioning," the disclosure of which is incorporated herein by reference.

The invention further includes a method, as shown in FIG. 3, for using the device 10, 10' for endocrine and exocrine gland control. The method begins at step 22 by selecting one or more stored neuro-electrical coded signals from a menu of cataloged neuro-electrical coded signals. The neuro-electrical coded signals selected activate, deactivate, secrete, or adjust the endocrine and exocrine glands. Such neuro-electrical coded signals are similar to those naturally produced by the brain structures for balancing and controlling glandular processes. Once selected, the neuro-electrical coded signals may be adjusted, in step 24, to perform a particular function in the body. Alternatively, if it is decided that the neuro-electrical coded signals do not need to be adjusted, step 24 is skipped and the process proceeds directly with step 26. At step 26, the neuro-electrical coded signal is transmitted to the treatment member 12, 12' of the device 10, 10'.

Upon receipt of the neuro-electrical coded signals, the treatment member 12, 12' broadcasts the neuro-electrical coded signals to the endocrine and exocrine glands or nerve location, as shown in step 28. The device 10, 10' utilizes appropriate neuro-electrical coded signals to adjust or modulate glandular action via conduction or broadcast of neuro-electrical coded signals into selected nerves. Controlling endocrine and exocrine gland function may require sending neuro-electrical coded signals into one or more nerves, including up to ten nerves simultaneously. It is believed that target glands can only "respond" to their own individual neuro-electrical coded signal.

In one embodiment of the invention, the process of broadcasting by the treatment member 12, 12' is accomplished by direct conduction or transmission through unbroken skin in a selected appropriate zone on the neck, head, limb(s), spine, thorax, or abdomen. Such zone will approximate a position close to the nerve or nerve plexus onto which the signal is to be imposed. The treatment member 12, 12' is brought into contact with the skin in a selected target area that allows for the transport of the signal to the target nerve(s).

In an alternate embodiment of the invention, the process of broadcasting the neuro-electrical coded signal is accomplished by direct conduction via attachment of an electrode to the receiving nerve or nerve plexus. This requires a surgical intervention as required to physically attach the electrode to the selected target nerve. Direct implantation on the nervous system of the selected endocrine and exocrine glands may be performed in order to transmit signals to control all or some glandular function. Such implantation can be pre-synaptic or post-synaptic and may be attached to ganglion or nerve plexus associated with the desired secretion function.

In yet another embodiment of the invention, the process of broadcasting is accomplished by transposing the neuro-electrical coded signal into a seismic form where it is sent into a region of the head, neck, limb(s), spine, or thorax in a manner that allows the appropriate "nerve" to receive and to obey the coded instructions of such seismic signal. The treatment member 12, 12' is pressed against the unbroken skin surface using an electrode conductive gel or paste medium to aid conductivity.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A method for controlling endocrine and exocrine glands, said method comprising:
   collecting neuro-electrical coded signals generated in a body and indicative of endocrine gland and exocrine gland functioning and carried by nerves in said body;
   converting said neuro-electrical coded signals into digital signals via an analog-to-digital converter;
   recording into a computer memory, said neuro-electrical coded signals generated in said body and indicative of said endocrine gland and said exocrine gland functioning, wherein said neuro-electrical coded signals are recorded in said computer memory as said digital signals;
   converting said neuro-electrical coded signals from said digital signals into analog signals via a digital-to-analog converter;
   transmitting or conducting selected waveforms of said neuro-electrical coded signals as said analog signals to a treatment member in contact with a body, wherein said treatment member comprises a seismic transducer
   broadcasting the selected waveforms of said neuro-electrical coded signals from the treatment member to an area in the body that is affected to control endocrine and/or exocrine glands in said body;
   selecting waveforms for selection as said selected waveforms from said computer memory, wherein said selected waveforms comprise analog signals converted from said digital signals to said analog signals via said digital-to-analog converter; and initiating a seismic transmission of the selected waveforms.

2. The method of claim 1 further comprising transmitting the selected waveforms remotely to the treatment member.

3. The method of claim 2 further comprising adjusting glandular action in the body via conduction or broadcast of said selected waveforms from the treatment member to said area in the body that is affected to control said endocrine and/or exocrine glands.

4. The method of claim 2 wherein said treatment member comprises an antenna.

5. The method of claim 1 wherein said treatment member comprises an electrode.

6. The method of claim 1 wherein said transmitting or conducting said selected waveforms to said treatment member in contact with said body occurs with a current less than 2 amps output.

7. The method of claim 1 wherein said transmitting or conducting said selected waveforms to said treatment member in contact with said body occurs to induce direct conduction into nerves of said body have output of less than 3 volts and a current of less than one-tenth of an amp.

8. A system for controlling endocrine and exocrine glands, said system comprising:

a processor; and a non-transitory computer-usable medium embodying computer program code, said computer-usable medium capable of communicating with said processor, said computer program code comprising instructions executable by said processor and configured for:

collecting neuro-electrical coded signals generated in a body and indicative of endocrine gland and exocrine gland functioning and carried by nerves in said body;

converting said neuro-electrical coded signals into digital signals via an analog-to-digital converter;

recording into a computer memory, said neuro-electrical coded signals generated in said body and indicative of said endocrine gland and said exocrine gland functioning, wherein said neuro-electrical coded signals are recorded in said computer memory as said digital signals;

converting said neuro-electrical coded signals from said digital signals into analog signals via a digital-to-analog converter;

transmitting or conducting selected waveforms of said neuro-electrical coded signals as said analog signals to a treatment member in contact with a body, said treatment member comprising a seismic transducer broadcasting the selected waveforms of said neuro-electrical coded signals from the treatment member to an area in the body that is affected to control endocrine and/or exocrine glands in said body selecting waveforms for selection as said selected waveforms from said computer memory, wherein said selected waveforms comprise analog signals converted from said digital signals to said analog signals via said digital-to-analog converter; and initiating a seismic transmission of the selected waveforms.

9. The system of claim 8 wherein said instructions are further configured for transmitting the selected waveforms remotely to the treatment member.

10. The system of claim 9 wherein said treatment member comprises an antenna.

11. The system of claim 8 wherein said treatment member comprises an electrode.

12. The system of claim 8 wherein said treatment member is attached to efferent nerves leading to said endocrine and/or exocrine glands in said body.

13. The system of claim 8 wherein said instructions are further configured for adjusting glandular action in the body via conduction or broadcast of said selected waveforms from the treatment member to said area in the body that is affected to control said endocrine and/or exocrine glands.

14. The system of claim 8 wherein said treatment member is attached to afferent nerves leading to the brain or brainstem of said body to accomplish a modulation of glandular output with respect to said endocrine and/or exocrine glands in said body.

* * * * *